United States Patent
Vaporciyan et al.

(10) Patent No.: US 10,308,586 B2
(45) Date of Patent: Jun. 4, 2019

(54) USE OF COMPOSITION COMPRISING TITANIUM OR ZIRCONIUM ALKOXIDE OR ARYLOXIDE IN AROMATIC CARBONATE PREPARATION PROCESS

(71) Applicant: SHELL OIL COMPANY, Houston, TX (US)

(72) Inventors: Garo Garbis Vaporciyan, Houston, TX (US); Kunquan Yu, Katy, TX (US)

(73) Assignee: Shell Oil Company, Houston, TX (US)

( * ) Notice: Subject to any disclaimer, the term of this patent is extended or adjusted under 35 U.S.C. 154(b) by 2 days.

(21) Appl. No.: 15/543,272

(22) PCT Filed: Jan. 14, 2016

(86) PCT No.: PCT/EP2016/050600
§ 371 (c)(1),
(2) Date: Jul. 13, 2017

(87) PCT Pub. No.: WO2016/113323
PCT Pub. Date: Jul. 21, 2016

(65) Prior Publication Data
US 2017/0369415 A1    Dec. 28, 2017

(30) Foreign Application Priority Data

Jan. 15, 2015    (EP) .................................... 15151212

(51) Int. Cl.
| | | |
|---|---|---|
| *C08G 64/06* | (2006.01) | |
| *C07C 68/06* | (2006.01) | |
| *C08G 64/30* | (2006.01) | |
| *B01J 31/22* | (2006.01) | |
| *B01J 31/02* | (2006.01) | |

(52) U.S. Cl.
CPC ............ *C07C 68/06* (2013.01); *B01J 31/2226* (2013.01); *C08G 64/06* (2013.01); *C08G 64/307* (2013.01); *B01J 31/0202* (2013.01); *B01J 31/0212* (2013.01); *B01J 31/0214* (2013.01); *B01J 2231/49* (2013.01); *B01J 2531/46* (2013.01); *B01J 2531/48* (2013.01)

(58) Field of Classification Search
USPC .................................................. 528/196, 198
See application file for complete search history.

(56) References Cited

U.S. PATENT DOCUMENTS

| | | |
|---|---|---|
| 5,747,609 A | 5/1998 | Komiya et al. |
| 2012/0316357 A1 | 12/2012 | Nishiyama et al. |

FOREIGN PATENT DOCUMENTS

| | | | |
|---|---|---|---|
| EP | 0780361 A1 | 6/1997 | |
| EP | 1837328    * | 9/2007 | ............ C07C 68/07 |
| EP | 2540694 A1 | 1/2013 | |
| WO | 2005026235 A1 | 3/2005 | |
| WO | 2009010486 A1 | 1/2009 | |
| WO | 2011067263 A1 | 6/2011 | |

OTHER PUBLICATIONS

International Search Report and Written Opinion received for PCT Patent Application No. PCT/EP2016/050600, dated Apr. 1, 2016, 9 pages.
Day et al., "Isolation and Structural Characterization of Tetra-n-propyl Zirconate in Hydrocarbon Solution and the Solid State", American Chemical Society, Inorganic Chemistry, vol. 40, Issue No. 23, Jul. 20, 2001, pp. 5738-5746.
Ibers, "Crystal and Molecular Structure of Titanium (IV) Ethoxide", Nature, vol. 197, Issue No. 4868, Feb. 16, 1963, p. 686.

* cited by examiner

*Primary Examiner* — Terressa Boykin

(57) ABSTRACT

The invention relates to a process for preparing an aromatic carbonate, comprising reacting a dialkyl carbonate or an alkyl aryl carbonate with an aryl alcohol or an alkyl aryl carbonate, resulting in an aromatic carbonate which is an alkyl aryl carbonate or a diaryl carbonate.

12 Claims, No Drawings

USE OF COMPOSITION COMPRISING TITANIUM OR ZIRCONIUM ALKOXIDE OR ARYLOXIDE IN AROMATIC CARBONATE PREPARATION PROCESS

PRIORITY CLAIM

The present application is the National Stage (§ 371) of International Application No. PCT/EP2016/050600, filed Jan. 14, 2016, which claims priority from European Patent Application No. 15151212.6, filed Jan. 15, 2015 incorporated herein by reference.

FIELD OF THE INVENTION

The present invention relates to a process for preparing an aromatic carbonate, such as a diaryl carbonate, using a composition comprising a titanium or zirconium alkoxide or aryloxide; and to a process for making a polycarbonate from the diaryl carbonate thus prepared.

BACKGROUND OF THE INVENTION

It is known that titanium and zirconium alkoxides and aryloxides may become a solid at ambient temperature and pressure. For example, when freshly distilled, titanium tetraethoxide (Ti(OEt)$_4$) is a colourless liquid in the standard state, that is to say at a standard temperature of 25° C. and a standard pressure of 100 kPa. However, in the standard state, liquid titanium tetraethoxide converts to a solid, crystalline mass over time (J. A. Ibers, "Crystal and Molecular Structure of Titanium (IV) Ethoxide", Nature 197 (4868): 686, 1963). This is also observed at ambient temperature, which may for example be of from −10 to +25° C., for other titanium alkoxides or aryloxides, such as titanium tetramethoxide, titanium tetra(n-propoxide), titanium tetraisopropoxide and titanium tetraphenoxide.

The foregoing also applies to zirconium alkoxides and aryloxides such as for example Zr(OEt)$_4$ and Zr(O"Pr)$_4$ (V. W. Day et al., "Isolation and Structural Characterization of Tetra-n-propyl Zirconate in Hydrocarbon Solution and the Solid State", Inorganic Chemistry 40 (23): 5738-46, 2001).

Ti(OMe)$_4$, Ti(OPh)$_4$ and Ti(OEt)$_4$ have relatively high melting temperatures of 200-210° C., 154° C. and 54° C., respectively, so that these exist as a solid in the standard state (at 25° C. and 100 kPa). In case the alkyl groups are isopropyl or n-propyl groups, as in Ti(O$^i$Pr)$_4$ and Ti(O"Pr)$_4$, respectively, which have melting temperatures of 17° C. and 20° C., respectively, a liquid does exist in the standard state. However, when the temperature is reduced to a temperature below these melting temperatures, for example during transport and/or storage, these liquid titanium tetrapropoxides would solidify.

Titanium or zirconium alkoxides or aryloxides may be used as catalysts in a variety of chemical production processes. For example, a titanium or zirconium alkoxide or aryloxide may be used as a catalyst in an aromatic carbonate production process. It is known to produce aromatic carbonates from a dialkyl carbonate and an aryl alcohol. For example, the aromatic carbonate may be a diaryl carbonate, such as diphenyl carbonate, which may be prepared from a dialkyl carbonate and an aryl alcohol. In such processes, the dialkyl carbonate is converted into diaryl carbonate via the following steps. In a first step, transesterification of the dialkyl carbonate with the aryl alcohol takes place to yield alkyl aryl carbonate (also an aromatic carbonate) and alkyl alcohol. In a second step, disproportionation of the alkyl aryl carbonate takes place to yield diaryl carbonate and dialkyl carbonate. Further transesterification of the alkyl aryl carbonate with aryl alcohol yielding diaryl carbonate and alkyl alcohol may also take place.

In a chemical production process wherein one of the above-described titanium or zirconium alkoxides or aryloxides having a relatively high melting temperature is employed as a catalyst, in order to hold the titanium or zirconium alkoxide or aryloxide in a molten state, a relatively high temperature has to be employed, for example higher than 55° C. in case above-mentioned titanium tetraethoxide is used. First of all, this imposes an undesired substantial energy requirement. Furthermore, when titanium or zirconium alkoxide or aryloxide is held in a molten state at such a high temperature for a long period of time, it starts being colored, and if it is used as a starting material for producing aromatic carbonates, the color tone of the obtained product tends to be impaired, and the product cannot be used as an ordinary aromatic carbonate product.

Furthermore, the heat stability of titanium or zirconium alkoxide or aryloxide at said relatively high temperature is relatively low. This for example results in that in a case where any moisture (water) is present, the titanium or zirconium alkoxide or aryloxide may easily react with such water at a high temperature. This is illustrated hereinbelow with reference to titanium alkoxide:

Ti(OR)$_4$+4H$_2$O→Ti(OH)$_4$+4ROH (hydrolysis)

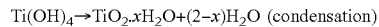

Ti(OH)$_4$→TiO$_2$.xH$_2$O+(2−x)H$_2$O (condensation)

Thus, said reaction results in the production of titanium dioxide of formula TiO$_2$, also known as titanium(IV) oxide or titania. The presence of such TiO$_2$ is disadvantageous as it has little to no catalytic activity, more especially in the above-mentioned process for preparing aromatic carbonates from a dialkyl carbonate and an aryl alcohol. Therefore, it is desirable to prevent the formation of TiO$_2$, and therefore the loss of valuable Ti metal, as much as possible. Furthermore, TiO$_2$ is a powder that is not soluble in most solvents. Therefore, another disadvantage of TiO$_2$ formation is that this powder covers the surface of any heterogeneous catalyst thereby blocking access to catalyst pores. In summary, said reaction with water may result in a catalyst the activity of which may be far less than the desired activity level.

Furthermore, titanium and zirconium alkoxides can undergo a condensation reaction even in the absence of moisture, especially after a prolonged period of time of heating. This is illustrated hereinbelow with reference to titanium alkoxide:

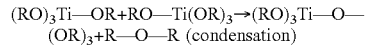

(RO)$_3$Ti—OR+RO—Ti(OR)$_3$→(RO)$_3$Ti—O—(OR)$_3$+R—O—R (condensation)

This condensation reaction is disadvantageous, as the Ti—O—Ti containing compound is less catalytically active but also has a melting temperature which is even higher than that of Ti(OR)$_4$.

In addition, most standard transport vessels for liquid materials are not equipped to maintain a temperature above 70° C. However, safe transport and handling of molten titanium or zirconium alkoxide or aryloxide (e.g. with minimal waste from tank washings) requires maintaining the product at a temperature of preferably about 20° C. above the melting point. Transport of liquid materials at such temperature would require a large amount of energy, and could lead to problems with solidifying material if not properly handled. Only a limited number of vessels are even capable of such proper handling at these temperatures, all with rather small tank sizes.

Thus, in view of the above problems associated with a relatively high temperature to keep titanium or zirconium alkoxide or aryloxide in a molten state, it would be better to transport and store titanium or zirconium alkoxide or aryloxide as a solid at ambient conditions. However, this in turn is also problematic. For example, it is problematic to transport solid titanium or zirconium alkoxide or aryloxide catalyst to a chemical production location and to store it at such location in the solid state. For example, in a case where solid titanium or zirconium alkoxide or aryloxide would be handled as a powder, the powder would easily block for example a piping of an apparatus or dissolution in a solvent may be impaired. Therefore, it would be difficult to continue a continuous operation using solid titanium or zirconium alkoxide or aryloxide for a long time, and the operation would have to be stopped repeatedly for washing apparatus such as a conveyer, thus leading to a considerable production loss.

The handling and transport of solid titanium or zirconium alkoxide or aryloxide have drawbacks common to handling of solids in general. Further, in particular, solid titanium or zirconium alkoxide or aryloxide is sensitive to moisture and will then hydrolyze readily, as described above with reference to $Ti(OR)_4$. Therefore, solid titanium or zirconium alkoxide or aryloxide should be handled and transported under a dry nitrogen environment. Having to provide and maintain such dry nitrogen environment is cumbersome.

Thus, the transport of titanium or zirconium alkoxide or aryloxide in the solid state requires the titanium or zirconium alkoxide or aryloxide to be solidified after its production. This is usually accomplished by allowing the titanium or zirconium alkoxide or aryloxide to form a solid and by forming it into suitable particles, which can then be bagged and transported as solid material. Generally, such solidification and particle formation require large and complicated equipment. Alternatively, titanium or zirconium alkoxide or aryloxide can be stored and solidified in special vessels after its production and then re-melted at the time of use. However, this also requires complicated equipment, like special vessels which either have self-heating capability or can be heated up in for example a hot room.

Such large and complicated equipment unnecessarily increases the capital investment, and is expensive and energy consuming to operate. Therefore, it is generally an object not to have to store and transport titanium or zirconium alkoxide or aryloxide in the solid state.

In view of the above, there is a need to decrease the holding temperature of titanium or zirconium alkoxide or aryloxide, such that titanium or zirconium alkoxide or aryloxide can be held as a liquid at a relatively low temperature. In that way, titanium or zirconium alkoxide or aryloxide catalyst could be advantageously transported and stored in liquid form at a relatively low temperature without having the above-mentioned drawbacks.

One solution to achieve this is to blend different titanium or zirconium alkoxides or aryloxides. For example, in case the desired catalyst to be used is $Ti(OEt)_4$, this may be blended with for example 3-20 wt. % of $Ti(O^iPr)_4$ such that the resulting blend is a liquid in the standard state (at 25° C. and 100 kPa). Such liquid blends are commercially available. For example, Santa Cruz Biotechnology, Inc. markets sc-251257, a product that contains 80-97% of titanium(IV) ethoxide and 3-20% of titanium(IV) isopropoxide. Further, Sigma-Aldrich markets Aldrich-244759, a technical grade titanium ethoxide product that contains about 80% titanium (IV) ethoxide and about 20% titanium(IV) isopropoxide. However, said blends may still solidify if the temperature is reduced from the standard state temperature of 25° C. to a relatively low temperature, which may be as low as −10° C. or even lower, which temperature reduction could occur during transport and/or storage of these blends.

Further, a drawback of such blending, in a case where the catalyst is to be used in a process wherein aromatic carbonates are produced from a dialkyl carbonate and an aryl alcohol, is that alcohol impurities would be introduced into the process. For example, in a case where diethyl carbonate is reacted with an aryl alcohol, first ethyl aryl carbonate and ethanol are formed. If in such case, a blend of $Ti(OEt)_4$ with $Ti(O^iPr)_4$ is used as a catalyst, a certain amount of isopropanol would be formed through the following general ligand exchange reaction (R=ethyl or isopropyl):

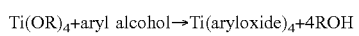

$$Ti(OR)_4 + aryl\ alcohol \rightarrow Ti(aryloxide)_4 + 4ROH$$

This isopropanol impurity would then mix with the larger amount of ethanol. The formation of such alcohol mixture is disadvantageous in case the ethanol is to be recycled for example to a preceding step wherein further diethyl carbonate is to be made using such recycled ethanol (e.g. by reacting that ethanol with ethylene carbonate resulting in diethyl carbonate and monoethylene glycol), in which case the isopropanol first needs to be separated from the alcohol mixture, which is cumbersome. In addition, the isopropanol formed may react with the carbonates fed to and/or formed in the aromatic carbonate production process to form corresponding carbonates which would also disadvantageously contaminate product and process streams and thus complicate purification.

Therefore, it is an object of the present invention to find a way wherein said problems associated with handling solid titanium or zirconium alkoxide or aryloxide as well as said problems associated with handling titanium or zirconium alkoxide or aryloxide at a relatively high temperature to maintain it in a liquid state, are avoided or decreased, without having to blend in any other titanium or zirconium alkoxide or aryloxide as discussed above.

SUMMARY OF THE INVENTION

Surprisingly, it was found that the above-mentioned object may be achieved by providing the titanium or zirconium alkoxide or aryloxide in combination with 0.1 to 50 wt. % of an alcohol. Surprisingly and advantageously, such combination may reduce the melting temperature of the titanium or zirconium alkoxide or aryloxide, such that the titanium or zirconium alkoxide or aryloxide can be held as a liquid at a relatively low temperature, thereby enabling transport and storage of titanium or zirconium alkoxide or aryloxide catalyst in liquid form at a relatively low temperature.

Accordingly, the present invention relates to a process for preparing an aromatic carbonate, comprising reacting a dialkyl carbonate or an alkyl aryl carbonate with an aryl alcohol or an alkyl aryl carbonate, resulting in an aromatic carbonate which is an alkyl aryl carbonate or a diaryl carbonate, wherein a composition comprising a titanium or zirconium alkoxide or aryloxide, wherein the alkoxy group in the titanium or zirconium alkoxide is a group of formula R—O⁻ wherein R is an alkyl group having 1 to 4 carbon atoms and the aryloxy group in the titanium or zirconium aryloxide is a group of formula Ar—O⁻ wherein Ar is an aryl group having 6 to 12 carbon atoms, and wherein the composition additionally comprises 0.1 to 50 wt. % of an alcohol, based on the total weight of the composition, is mixed with an alcohol or an organic carbonate, and the mixture thus obtained is contacted with said dialkyl carbonate or alkyl aryl carbonate and aryl alcohol or alkyl aryl carbonate to catalyze the preparation of the aromatic carbonate.

Thus, through being a liquid at a relatively low temperature, the titanium or zirconium alkoxide or aryloxide composition used in the present invention may be stored and handled (including transport) in a greatly simplified way. And the shelf life of that titanium or zirconium alkoxide or aryloxide composition may be significantly extended. Furthermore, being a liquid means that it may be directly fed into a process wherein it is to be used, by applying a pump which again simplifies its use.

Further, the composition comprising a combination of titanium or zirconium alkoxide or aryloxide with 0.1 to 50 wt. % of an alcohol is advantageous in that said alcohol can be chosen such that it corresponds to any alcohol used and/or produced in a subsequent chemical production process wherein the titanium or zirconium alkoxide or aryloxide is used as a catalyst. In that way, advantageously, by first combining the titanium or zirconium alkoxide or aryloxide with such alcohol, no new chemicals are introduced into the subsequent chemical production process. For example, in a case where the subsequent chemical production process concerns the preparation of diaryl carbonate from diethyl carbonate and aryl alcohol through the intermediate formation of ethyl aryl carbonate, wherein ethanol is liberated, titanium or zirconium alkoxide or aryloxide may be combined, before use as a catalyst, with ethanol and/or aryl alcohol, preferably ethanol.

Further, the present invention relates to a process for making a polycarbonate from a diaryl carbonate prepared in accordance with the aromatic carbonate preparation process of the present invention.

DETAILED DESCRIPTION OF THE INVENTION

The composition used in the present invention comprises a titanium or zirconium alkoxide or aryloxide, wherein the alkoxy group in the titanium or zirconium alkoxide is a group of formula R—O$^-$ wherein R is an alkyl group having 1 to 4 carbon atoms and the aryloxy group in the titanium or zirconium aryloxide is a group of formula Ar—O$^-$ wherein Ar is an aryl group having 6 to 12 carbon atoms.

While any processes and/or compositions embodying the present invention are described in terms of "comprising", "containing" or "including" various described features and/or steps, they can also "consist essentially of" or "consist of" the various described features and steps. Thus, while the composition and processes of the present invention are described in terms of "comprising", "containing" or "including" one or more various described components and steps, respectively, they can also "consist essentially of" or "consist of" said one or more various described components and steps, respectively.

Within the present specification, said titanium or zirconium alkoxide or aryloxide means a titanium or zirconium containing compound which, in addition to the metal, contains one or more ligands, which may be the same or different, wherein one or more of the ligands is or are an alkoxy group and/or an aryloxy group and wherein any remaining ligands are selected from the group consisting of arylalkoxy, alkylaryloxy, alkyl, arylalkyl, aryl, alkylaryl, hydroxide, carboxylate, carbonate and halide groups. Preferably, all of said ligands are the same and are an alkoxy group and/or an aryloxy group, more preferably an alkoxy group or an aryloxy group. More preferably, the titanium or zirconium alkoxide is of formula M(OR)$_4$, wherein M=Ti or Zr, most preferably Ti, and wherein R is an alkyl group having 1 to 4 carbon atoms, whereas the titanium or zirconium aryloxide is of formula M(OAr)$_4$, wherein M=Ti or Zr, most preferably Ti, and wherein Ar is an aryl group having 6 to 12 carbon atoms.

Within the present specification, an "arylalkoxy" group is a group of formula Ar—R—O$^-$ wherein Ar is an aryl group and R is an alkyl group. An "aryloxy" group is a group of formula Ar—O$^-$ wherein Ar is an aryl group. An "alkylaryloxy" group is a group of formula R—Ar—O$^-$ wherein R is an alkyl group and Ar is an aryl group. An "alkyl" group is of formula R. An "arylalkyl" group is a group of formula Ar—R wherein Ar is an aryl group and R is an alkyl group. An "aryl" group is a group of formula Ar. An "alkylaryl" group is a group of formula R—Ar wherein R is an alkyl group and Ar is an aryl group. A "hydroxide" group is a group of formula HO$^-$. A carboxylate group is a group of formula R'—C(=O)—O$^-$ wherein R' may be an alkyl, arylalkyl, aryl or alkylaryl group. For example, said carboxylate group may be an acetoxy group. A carbonate group is a group of formula $^-$O—C(=O)—O$^-$. These alkyl and aryl groups may be substituted or unsubstituted. Further, the alkyl group may be a branched or linear, preferably linear, $C_1$-$C_6$ alkyl group, preferably $C_1$-$C_4$ alkyl group, more preferably $C_1$-$C_3$ alkyl group (methyl, ethyl, n-propyl or isopropyl group), more preferably $C_1$-$C_2$ alkyl group (methyl or ethyl group), most preferably $C_2$ alkyl group (ethyl group). The aryl group may be a phenyl group. A halide group may be selected from the group consisting of fluoride (F$^-$), chloride (Cl$^-$), bromide (Br$^-$) and iodide (I$^-$).

Preferably, said alkyl group for the alkoxy group in the titanium or zirconium alkoxide which may be contained in the composition used in the present invention, has 1 to 3 carbon atoms. Further, preferably, said alkyl group is selected from the group consisting of methyl, ethyl, n-propyl and isopropyl, more preferably from the group consisting of ethyl, n-propyl and isopropyl, most preferably from the group consisting of ethyl and isopropyl. If the alkyl group is n-propyl, the oxygen atom is bonded to the first, primary carbon atom of the propyl group. If the alkyl group is isopropyl, the oxygen atom is bonded to the second, secondary carbon atom of the propyl group. More preferably, said alkyl group is selected from the group consisting of methyl, ethyl and n-propyl. Even more preferably, said alkyl group is methyl or ethyl. Most preferably, said alkyl group is ethyl. As mentioned above, preferably, the titanium or zirconium alkoxide is of formula M(OR)$_4$, wherein M=Ti or Zr, most preferably Ti, and wherein R is said alkyl group. Most preferably, the composition used in the present invention comprises titanium tetraethoxide.

In the present invention, the aryloxy group in the titanium or zirconium aryloxide is a group of formula Ar—O$^-$ wherein Ar is an aryl group having 6 to 12 carbon atoms. Preferably, said aryl group is phenyl. As mentioned above, preferably, the titanium or zirconium aryloxide is of formula M(OAr)$_4$, wherein M=Ti or Zr, most preferably Ti, and wherein Ar is said aryl group. A particular suitable example of a titanium or zirconium aryloxide is titanium tetraphenoxide.

In addition to the above-described titanium or zirconium alkoxide or aryloxide, the composition used in the present invention comprises an alcohol. It has surprisingly appeared that by adding an alcohol to a titanium or zirconium alkoxide or aryloxide, the melting temperature of the resulting composition (blend) is reduced as compared to the melting point of the titanium or zirconium alkoxide or aryloxide alone, such that the composition can be held as a liquid at a relatively low temperature, thereby enabling transport and storage of titanium or zirconium alkoxide or aryloxide catalyst in liquid form at a relatively low temperature.

Preferably, the alcohol is an alcohol which is a liquid in the standard state, that is to say at a standard temperature of 25° C. and a standard pressure of 100 kPa.

As to the chemical composition of the alcohol, any alcohol may be used. The alcohol may be an alkyl alcohol or an aryl alcohol. An aryl alcohol may be used which is of formula Ar—OH wherein Ar is an aryl group having 6 to 12 carbon atoms. For example, said aryl alcohol may be phenol. Preferably, the alcohol is an alkyl alcohol. An alkyl alcohol may be used which is of formula R—OH wherein R is an alkyl group having 1 to 4 carbon atoms, suitably 1 to 3 carbon atoms. Said alkyl group may be linear or branched, preferably linear. Suitable examples of alkyl alcohols are methanol, ethanol, n-propanol, isopropanol, n-butanol, sec-butanol, isobutanol and t-butanol. Preferably, the alkyl alcohol is selected from the group consisting of methanol, ethanol, n-propanol and isopropanol. More preferably the alkyl alcohol is methanol or ethanol, most preferably ethanol. Further, suitably, the alkyl alcohol is selected from the group consisting of ethanol, n-propanol and isopropanol, or from the group consisting of ethanol and isopropanol.

The amount of the alcohol in the composition used in the present invention is not essential and is 0.1 to 50 wt. %, based on the total weight of the composition. Accordingly, the composition used in the present invention may comprise 50 to 99.9 wt. % of the titanium or zirconium alkoxide or aryloxide, based on the total weight of the composition. Preferably, the composition used in the present invention comprises 0.1 to 20 wt. %, more preferably 0.5 to 10 wt. %, most preferably 1 to 6 wt. % of the alcohol, based on the total weight of the composition. Accordingly, the composition used in the present invention preferably comprises 70 to 99.9 wt. %, more preferably 90 to 99.5 wt. %, most preferably 94 to 99 wt. % of the titanium or zirconium alkoxide or aryloxide, based on the total weight of the composition. The minimum amount of alcohol needed to keep the composition used in the present invention as a liquid depends on the temperature at which said composition is to be transported and/or stored. The lower said temperature, the more alcohol is needed. Furthermore, this depends on the nature of the alcohol.

The amount of the alcohol in the composition used in the present invention is at least 0.1 wt. %, based on the total weight of the composition, preferably at least 0.5 wt. %, more preferably at least 1 wt. %, more preferably at least 1.5 wt. %, more preferably at least 2 wt. %, more preferably at least 2.5 wt. %, more preferably at least 3 wt. %, more preferably at least 3.5 wt. %, more preferably at least 4 wt. %, more preferably at least 4.5 wt. %, most preferably at least 5 wt. %. Further, said amount may be at least 6 wt. %, or at least 7 wt. %, or at least 8 wt. %.

The amount of the alcohol in the composition used in the present invention is at most 50 wt. %, based on the total weight of the composition, preferably at most 40 wt. %, more preferably at most 30 wt. %, more preferably at most 25 wt. %, more preferably at most 20 wt. %, more preferably at most 15 wt. %, more preferably at most 10 wt. %, most preferably at most 8 wt. %. Further, said amount may be at most 7 wt. %, or at most 6 wt. %.

In the context of the present invention, in a case where a composition used in the present invention comprises two or more components, these components are to be selected in an overall amount not to exceed 100 wt. %.

The composition comprising a titanium or zirconium alkoxide or aryloxide, wherein the alkoxy group in the titanium or zirconium alkoxide is a group of formula R—O$^-$ wherein R is an alkyl group having 1 to 4 carbon atoms and the aryloxy group in the titanium or zirconium aryloxide is a group of formula Ar—O$^-$ wherein Ar is an aryl group having 6 to 12 carbon atoms, may be prepared by a process comprising blending the titanium or zirconium alkoxide or aryloxide with an alcohol in such amounts that the resulting composition comprises 0.1 to 50 wt. % of the alcohol, based on the total weight of the composition.

The composition used in the present invention comprising a titanium or zirconium alkoxide or aryloxide and an alcohol may be prepared in any way. For example, solid titanium or zirconium alkoxide or aryloxide may be converted to liquid titanium or zirconium alkoxide or aryloxide by heating, before blending with the alcohol. Alternatively, solid titanium or zirconium alkoxide or aryloxide may be blended with the alcohol, followed by heating to obtain a liquid composition. The foregoing 2 options may be applicable if titanium or zirconium alkoxide or aryloxide has solidified after it has been manufactured. However, the composition used in the present invention may also be prepared in the last phase of the process for manufacturing the titanium or zirconium alkoxide or aryloxide, for example when it is still a liquid directly after it has been manufactured (e.g. freshly distilled). For example, the composition may be prepared by blending liquid titanium or zirconium alkoxide or aryloxide with the alcohol. Preferably, the composition used in the present invention is prepared at the manufacturing site where the titanium or zirconium alkoxide or aryloxide is manufactured, so that a liquid blend can be made prior to transport and/or storage thereof. Additionally, as titanium and zirconium alkoxides are typically manufactured by reacting the tetrachloride of titanium or zirconium with an alcohol to give the corresponding titanium or zirconium tetraalkoxide, an excess of the alcohol may be used in this manufacturing process to yield a composition to be used in the present invention which comprises a titanium or zirconium alkoxide and said alcohol.

Thus, the present invention relates to a process for preparing an aromatic carbonate, comprising reacting a dialkyl carbonate or an alkyl aryl carbonate with an aryl alcohol or an alkyl aryl carbonate, resulting in an aromatic carbonate which is an alkyl aryl carbonate or a diaryl carbonate, wherein the above-mentioned composition comprising a titanium or zirconium alkoxide or aryloxide is mixed with an alcohol or an organic carbonate, and the mixture thus obtained is contacted with said dialkyl carbonate or alkyl aryl carbonate and aryl alcohol or alkyl aryl carbonate to catalyze the preparation of the aromatic carbonate.

The present invention also relates to a process for preparing an aromatic carbonate, comprising preparing a composition comprising a titanium or zirconium alkoxide or aryloxide in accordance with the above-mentioned process, mixing said composition with an alcohol or an organic carbonate and contacting the mixture thus obtained with a dialkyl carbonate or alkyl aryl carbonate and aryl alcohol or alkyl aryl carbonate to catalyze the preparation of the aromatic carbonate which is an alkyl aryl carbonate or a diaryl carbonate. The embodiments and preferences as described above with reference to the composition comprising a titanium or zirconium alkoxide or aryloxide and the process for preparing the same also apply to such composition used in and to such composition preparation step of, respectively, an aromatic carbonate preparation process of the present invention.

In the aromatic carbonate preparation process of the present invention, the alkyl group in the dialkyl carbonate and alkyl aryl carbonate may have 1 to 4, suitably 1 to 3 carbon atoms. Suitably, said alkyl group is a methyl group or ethyl group, more suitably an ethyl group. Further, in the aromatic carbonate preparation process of the present invention, the aryl group in the aryl alcohol, alkyl aryl carbonate and diaryl carbonate may have 6 to 12 carbon atoms. Preferably, said aryl group is a phenyl group. Therefore, preferably, said aryl alcohol is phenol and said diaryl carbonate is diphenyl carbonate. Suitable examples of said alkyl aryl carbonate are methyl phenyl carbonate and ethyl phenyl carbonate. Preferably, said dialkyl carbonate is of formula ROC(=O)OR', wherein R and R' may be the same or different and are $C_{1-4}$ alkyl groups, preferably $C_{1-3}$ alkyl groups. More preferably, said dialkyl carbonate is dimethyl carbonate or diethyl carbonate, most preferably diethyl carbonate. Further, preferably, in the aromatic carbonate preparation process of the present invention, a dialkyl carbonate is reacted with an aryl alcohol resulting in the corresponding alkyl aryl carbonate.

In the aromatic carbonate preparation process of the present invention, an alcohol may be mixed with the composition comprising a titanium or zirconium alkoxide or aryloxide, which alcohol may be an alkyl alcohol or an aryl alcohol. Preferably, said alcohol is an alkyl alcohol. An alkyl alcohol may be used which is of formula R—OH wherein R is an alkyl group having 1 to 4 carbon atoms, suitably 1 to 3 carbon atoms. If the alcohol is an aryl alcohol, it is preferably phenol. The embodiments and preferences as described above with reference to the alcohol as contained in the composition comprising a titanium or zirconium alkoxide or aryloxide used in the present invention also apply to the alcohol with which the latter composition may be mixed as part of the aromatic carbonate preparation process of the present invention. Preferably, the alcohol as contained in the composition comprising a titanium or zirconium alkoxide or aryloxide is the same as the alcohol with which said composition is mixed.

Further, in the aromatic carbonate preparation process of the present invention, an organic carbonate may be mixed with the composition comprising a titanium or zirconium alkoxide or aryloxide. As to the chemical composition of said organic carbonate, any organic carbonate may be used. For example, the organic carbonate may be a compound of formula ROC(=O)OR', wherein R and R' may be the same or different and are each an alkyl or aryl group, in particular a compound selected from the group consisting of dialkyl carbonates and alkyl aryl carbonates. Said alkyl group may have 1 to 4, suitably 1 to 3 carbon atoms. Suitably, said alkyl group is a methyl group or ethyl group, more suitably an ethyl group. Said aryl group may have 6 to 12 carbon atoms. Suitably, said aryl group is a phenyl group. Suitable examples of said alkyl aryl carbonate are methyl phenyl carbonate and ethyl phenyl carbonate. Preferably, said organic carbonate of formula ROC(=O)OR' is a dialkyl carbonate wherein R and R' are $C_{1-4}$ alkyl groups, preferably $C_{1-3}$ alkyl groups. More preferably, said dialkyl carbonate is dimethyl carbonate or diethyl carbonate, most preferably diethyl carbonate. Further, the organic carbonate may be a cyclic carbonate, like an alkylene carbonate, for example an alkylene carbonate having 3 to 6, suitably 3 to 4 carbon atoms. Suitable examples of alkylene carbonates are ethylene carbonate and propylene carbonate.

Generally, between preparing the composition comprising a titanium or zirconium alkoxide or aryloxide used in the present invention and the mixing thereof with an alcohol or an organic carbonate as part of the aromatic carbonate preparation process of the present invention, the composition comprising a titanium or zirconium alkoxide or aryloxide has to be transported to and optionally stored at the location of aromatic carbonate preparation. Therefore, suitably, the step of mixing an alcohol or an organic carbonate with the composition comprising a titanium or zirconium alkoxide or aryloxide is preceded by a step comprising transporting said composition, in particular transporting said composition to and/or at the location of aromatic carbonate preparation, for example to the location of aromatic carbonate preparation, and optionally storing said composition at such location. Such transport, like transporting at the location of aromatic carbonate preparation, for example covers transport of said composition from a storage tank to a reactor on the same site which transport may take place in a pipe. Further, suitably, the temperature during such transport and optionally storage is of from −10 to 50° C., preferably 0 to 40° C. In the present invention, the combination with an alcohol surprisingly and advantageously has resulted in a reduction of the melting temperature of the titanium or zirconium alkoxide or aryloxide, such that the titanium or zirconium alkoxide or aryloxide can be held as a liquid at a relatively low temperature, thereby enabling transport and storage of titanium or zirconium alkoxide or aryloxide catalyst in liquid form in a relatively broad temperature range.

To complete the conversion of a dialkyl carbonate and an aryl alcohol into a diaryl carbonate through the intermediate formation of an alkyl aryl carbonate, a series of two or three, preferably three, reactive distillation columns in total may be applied. The various embodiments as disclosed in above-mentioned WO2011067263, disclosing a process wherein three reactive distillation columns are used, may be applied to the present aromatic carbonate preparation process. The disclosure of WO2011067263 is herein incorporated by reference.

The pressures in said three reactive distillation columns may vary within wide limits. The pressure at the top of the first reactive distillation column may be 2 to 7 bar, preferably 2.5 to 5 bar. The pressure at the top of the second reactive distillation column may be 0.1 to 3 bar, preferably 0.3 to 1.5 bar. The pressure at the top of the third reactive distillation column may be 10 to 600 mbar, preferably 20 to 500 mbar. Preferably, the pressure at the top of the first reactive distillation column is higher than that of the second reactive distillation column which in turn is higher than that of the third reactive distillation column.

The temperatures in said three reactive distillation columns may also vary within wide limits. The temperature at the bottom of the first, second and third reactive distillation columns may be 50 to 350° C., preferably 120 to 280° C., more preferably 150 to 250° C., most preferably 160 to 240° C.

The catalyst in one or more of said three reactive distillation columns may be the titanium or zirconium alkoxide or aryloxide as contained in the composition comprising a titanium or zirconium alkoxide or aryloxide used in the present invention. This is a homogeneous catalyst. In addition, a heterogeneous catalyst may be used, especially in the first of these reactive distillation columns.

Still further, the present invention relates to a process for making a polycarbonate from a diaryl carbonate prepared in accordance with the aromatic carbonate preparation process of the present invention. Accordingly, the present invention relates to a process for making a polycarbonate, comprising reacting a dihydroxy aromatic compound with a diaryl carbonate prepared in accordance with the above-described aromatic carbonate preparation process. Further, accordingly, the present invention relates to a process for making a polycarbonate, comprising preparing a diaryl carbonate in accordance with the above-described aromatic carbonate preparation process, and reacting a dihydroxy aromatic compound with the diaryl carbonate thus obtained. The embodiments and preferences as described above with reference to the aromatic carbonate preparation process of the present invention also apply to said diaryl carbonate preparation step of the polycarbonate make process of the present invention.

Further, preferably, said dihydroxy aromatic compound is bisphenol A, which is 4,4'-(propan-2-ylidene)diphenol. The production of polycarbonate by the polymerisation of diaryl carbonate with an aromatic dihydroxy compound, such as bisphenol A, is well known. See for example U.S. Pat. No. 5,747,609, WO2005026235 and WO2009010486, the disclosures of which are herein incorporated by reference.

The invention is further illustrated by the following Examples.

EXAMPLES

In the present Examples, pure titanium tetraethoxide (Ti(OEt)$_4$; 99.7% purity as measured by TiO$_2$ content), which is a crystallized solid in the standard state and has a melting point of 54° C., was mixed with dry ethanol, said dry ethanol having a water content of less than 10 ppmw, at various Ti(OEt)$_4$:ethanol blend weight ratios. Then the solid/liquid phase behavior of the resulting blend was studied and monitored over time.

Before blending with the dry ethanol, the solid Ti(OEt)$_4$ was first heated to about 60° C. to fully melt it. Then the dry ethanol was added and after some mixing, the heating was stopped and the Ti(OEt)$_4$/ethanol blend was allowed to cool to ambient temperature (about 25° C.) or said blend was cooled to 0° C. or to −10° C. Then the solid/liquid phase behavior of the cooled Ti(OEt)$_4$:ethanol blend was monitored over time. As Ti(OEt)$_4$ is sensitive to moisture, all of the experiments were performed under a dry, inert environment. The observations made regarding the solid/liquid phase behavior of the blends over time are shown in Table 1 below (wherein EtOH=ethanol).

TABLE 1

| Blend ratio (wt. %) | | T | Observation solid/liquid phase behavior | | | |
|---|---|---|---|---|---|---|
| Ti(OEt)$_4$ | EtOH | (° C.) | 6 hours | 24 hours | 48 hours | 1 week |
| 100 | 0 | 25 | Hazy liquid | Solid | Solid | Solid |
| 99.0 | 1.0 | 25 | Clear liquid | Clear liquid | Clear liquid | Clear liquid |
| 96.0 | 4.0 | 25 | Clear liquid | Clear liquid | Clear liquid | Clear liquid |
| 94.0 | 6.0 | 0 | Clear liquid | Clear liquid | Clear liquid | Clear liquid |
| 92.0 | 8.0 | −10 | Clear liquid | Clear liquid | Clear liquid | Clear liquid |
| 90.0 | 10.0 | −10 | Clear liquid | Clear liquid | Clear liquid | Clear liquid |

From Table 1, it surprisingly appears that by adding only 1 wt. % of ethanol to Ti(OEt)$_4$, the resulting blend remains a homogeneous liquid in the standard state (at 25° C. and 100 kPa). Furthermore, it surprisingly appears that by adding more ethanol, the melting temperature of Ti(OEt)$_4$ can even be further lowered. For example, if only 6 wt. % of ethanol is added to Ti(OEt)$_4$, the resulting blend also remains a homogeneous liquid at the lower temperature of 0° C. Further, if only 8 wt. % of ethanol is added to Ti(OEt)$_4$, the resulting blend also remains a homogeneous liquid at the even lower temperature of −10° C.

The above-mentioned positive effect of an alcohol has also been shown for blends of isopropanol with Ti(O$^i$Pr)$_4$, which has a melting point of 17° C., applying the same experimental procedure as described above for the Ti(OEt)$_4$ containing blends. The results for the Ti(O$^i$Pr)$_4$ containing blends are shown in Table 2 below.

TABLE 2

| Blend ratio (wt. %) | | T | Observation solid/liquid phase behavior | |
|---|---|---|---|---|
| Ti(O$^i$Pr)$_4$ | isopropanol | (° C.) | 6 hours | 1 week |
| 100 | 0 | 25 | Clear liquid | Clear liquid |
| 100 | 0 | 17 | Hazy liquid | Solid |
| 94.0 | 6.0 | 5 | Clear liquid | Clear liquid |
| 90.0 | 10.0 | 0 | Clear liquid | Clear liquid |

From Table 2, it also surprisingly appears that by adding only 6 wt. % of isopropanol to Ti(O$^i$Pr)$_4$, the resulting blend also remains a homogeneous liquid at a temperature as low as 5° C. Furthermore, it surprisingly appears that by adding more isopropanol, the melting temperature of Ti(O$^i$Pr)$_4$ can even be further lowered. For example, if only 10 wt. % of isopropanol is added to Ti(O$^i$Pr)$_4$, the resulting blend also remains a homogeneous liquid at the lower temperature of 0° C.

Apart from the above surprising advantages, the addition of ethanol to Ti(OEt)$_4$ poses no problem in case the resulting catalyst composition is to be used in a chemical production process wherein for example a diaryl carbonate is prepared from diethyl carbonate and phenol. By adding ethanol to the Ti(OEt)$_4$, advantageously no new chemical would be introduced since ethanol is liberated (as a reaction product) in that chemical production process. The same would apply to a case wherein isopropanol is added to Ti(O$^i$Pr)$_4$, and the resulting catalyst composition is to be used in a chemical production process wherein for example a diaryl carbonate is prepared from diisopropyl carbonate and phenol.

That which is claimed is:

1. A process for preparing an aromatic carbonate, comprising reacting a dialkyl carbonate or an alkyl aryl carbonate with an aryl alcohol or an alkyl aryl carbonate, resulting in an aromatic carbonate which is an alkyl aryl carbonate or a diaryl carbonate, wherein a composition comprising a titanium or zirconium alkoxide, wherein the alkoxy group in the titanium or zirconium alkoxide is a group of formula R—O⁻ wherein R is selected from the group consisting of methyl, ethyl, n-propyl and isopropyl, and wherein the composition additionally comprises 0.1 to 50 wt. % of an alcohol, based on the total weight of the composition, is mixed with an alcohol or an organic carbonate, and the mixture thus obtained is contacted with said dialkyl carbonate or alkyl aryl carbonate and aryl alcohol or alkyl aryl carbonate to catalyze the preparation of the aromatic carbonate.

2. The process according to claim 1, wherein the amount of the alcohol in the composition, before mixing the composition with an alcohol or an organic carbonate, is 0.1 to 20 wt. %, based on the total weight of the composition.

3. The process according to claim 1, wherein the alcohol in the composition, before mixing the composition with an alcohol or an organic carbonate, is an alkyl alcohol or an aryl alcohol.

4. The process according to claim 3, wherein the alcohol in the composition, before mixing the composition with an alcohol or an organic carbonate, is an alkyl alcohol of formula R—OH wherein R is an alkyl group having 1 to 4 carbon atoms.

5. The process according to claim 4, wherein the alkyl alcohol is selected from the group consisting of methanol, ethanol, n-propanol and isopropanol.

6. The process according to claim 1, wherein an alcohol is mixed with the composition comprising a titanium or zirconium alkoxide, which alcohol is an alkyl alcohol or an aryl alcohol.

7. The process according to claim 6, wherein the alcohol is an alkyl alcohol of formula R—OH wherein R is an alkyl group having 1 to 4 carbon atoms.

8. The process according to claim 6, wherein the alcohol as contained in the composition comprising a titanium or zirconium alkoxide is the same as the alcohol with which said composition is mixed.

9. The process according to claim 1, wherein the step of mixing an alcohol or an organic carbonate with the composition comprising a titanium or zirconium alkoxide is preceded by a step comprising transporting said composition.

10. The A process according to claim 9, wherein the temperature during transport is of from −10 to 50° C.

11. The process for making a polycarbonate, comprising reacting a dihydroxy aromatic compound with a diaryl carbonate prepared in accordance with the process of claim 1.

12. The process for making a polycarbonate, comprising preparing a diaryl carbonate in accordance with the process of claim 1, and reacting a dihydroxy aromatic compound with the diaryl carbonate thus obtained.

* * * * *